(12) United States Patent
Bartholomäus et al.

(10) Patent No.: US 7,776,314 B2
(45) Date of Patent: Aug. 17, 2010

(54) ABUSE-PROOFED DOSAGE SYSTEM

(75) Inventors: Johannes Bartholomäus, Aachen (DE);
Heinrich Kugelmann, Aachen (DE)

(73) Assignee: Grunenthal GmbH, Aachen (DE)

( * ) Notice: Subject to any disclaimer, the term of this patent is extended or adjusted under 35 U.S.C. 154(b) by 673 days.

(21) Appl. No.: 11/007,887

(22) Filed: Dec. 9, 2004

(65) Prior Publication Data

US 2005/0152843 A1    Jul. 14, 2005

Related U.S. Application Data

(63) Continuation of application No. PCT/EP03/06314, filed on Jun. 16, 2003.

(30) Foreign Application Priority Data

Jun. 17, 2002 (DE) ............... 102 27 077
Oct. 25, 2002 (DE) ............... 102 50 083

(51) Int. Cl.
*A61K 49/00* (2006.01)
*A61K 9/48* (2006.01)
*A61K 9/20* (2006.01)
*A61K 9/14* (2006.01)
*A61K 9/16* (2006.01)

(52) U.S. Cl. ............... 424/10.1; 424/451; 424/464; 424/489; 424/490

(58) Field of Classification Search ............... 424/400
See application file for complete search history.

(56) References Cited

U.S. PATENT DOCUMENTS

| 3,980,766 A | 9/1976 | Shaw et al. ............... 424/10 |
| 4,070,494 A | 1/1978 | Hoffmeister et al. ............... 424/2 |
| 4,612,008 A | 9/1986 | Wong et al. ............... 604/892 |
| 4,765,989 A | 8/1988 | Wong et al. ............... 424/473 |
| 4,783,337 A | 11/1988 | Wong et al. ............... 424/468 |
| 6,228,863 B1 | 5/2001 | Palermo et al. ............... 514/282 |

FOREIGN PATENT DOCUMENTS

| DE | 25 30 563 | 1/1977 |
| EP | 0 693 475 | 1/1996 |
| EP | 0 780 369 | 6/1997 |
| WO | WO 95/20947 | 8/1995 |
| WO | 99/32120 | * 7/1999 |
| WO | WO 03/013476 | 2/2003 |

* cited by examiner

*Primary Examiner*—Humera N Sheikh
(74) *Attorney, Agent, or Firm*—Norris McLaughlin & Marcus PA

(57) ABSTRACT

The invention relates to a solid administration form, protected from parenteral abuse and containing at least one viscosity-increasing agent in addition to one or more active substances that have parenteral abuse potential. The agent forms, when a necessary minimum amount of an aqueous liquid is added, on the basis of an extract obtained from the administration form, a preferably injectable gel that remains visually distinct when introduced into another quantity of an aqueous liquid.

12 Claims, No Drawings

ABUSE-PROOFED DOSAGE SYSTEM

This application is a continuation of international application number PCT/EP03/06314 filed Jun. 16, 2003, status pending, and which claims priority to German Patent Applications DE 102 27 077.5 filed Jun. 17, 2002 and DE 102 50 083.5 filed Oct. 25, 2002.

The present invention relates to a solid dosage form with reduced parenteral abuse containing, in addition to one or more active ingredients with potential for abuse, at least one viscosity-increasing agent in quantities such that, on extraction with the assistance of a necessary minimum quantity of aqueous liquid, a gel is formed which can still preferably pass through a needle, which gel, however, remains visually distinguishable even after being introduced into a further quantity of an aqueous liquid.

Many pharmaceutical active ingredients, in addition to having excellent activity in their appropriate application, also have potential for abuse, i.e. they can be used by an abuser to bring about effects other than those intended. Opiates, for example, which are highly active in combating severe to very severe pain, are frequently used by abusers to induce a state of narcosis or euphoria.

Dosage forms which contain active ingredients with potential for abuse, even when taken orally in an abusively large quantity, do not usually give rise to the result desired by the abuser, namely a rapid rush or "kick", because blood levels of the active ingredients increase only slowly. In order nevertheless to achieve the desired effects and enable abuse, the corresponding dosage forms are comminuted, for example ground, by the abuser and the active ingredient is extracted from the powder obtained by comminution of the dosage form with the assistance of a preferably aqueous liquid, preferably the minimum quantity necessary, and the resultant solution, optionally after filtration through cotton wool or cellulose wadding, is administered parenterally, in particular intravenously. Due to this parenteral administration, only the smallest possible quantities of an aqueous liquid are used for extraction, in particular so as to obtain the smallest possible injection volume with active ingredient which results in the desired rapid rush or "kick". In this manner, parenteral administration, in comparison with oral administration, tends to give rise to an accelerated rise in levels of the active ingredient providing the abuser with the desired result.

In order to prevent this form of abuse, it has been proposed in U.S. Pat. No. 4,070,494 to prevent the extraction of an active ingredient from a dosage form by the addition of a swellable agent. On addition of water, this agent swells and ensures that only a small quantity of active ingredient containing liquid is obtained which can be administered parenterally by the abuser. The majority of this dosage form which has swollen is cannot be administered.

A corresponding approach to the prevention of parenteral abuse also underlies the multilayer tablet disclosed in WO 95120947 which contains the active ingredient with potential for abuse and one or more gel formers each in different layers.

According to this prior art teaching, the viscosity-increasing agents are added in quantities such that the corresponding gel cannot be administered with the assistance of conventional hypodermic needles.

The object of the present invention was to provide a dosage form with at least reduced potential for abuse for active ingredients having with such potential, which dosage form prevents any preferably still possible parenteral, in particular intravenous, abuse of the active ingredients.

This object has been achieved by the provision of the solid dosage form according to the invention with at least reduced potential for parenteral abuse, which dosage form, in addition to one or more active ingredients with potential for abuse, comprises at least one viscosity-increasing agent in a quantity such that a gel which may preferably still pass through a needle is formed in an extract obtained from the dosage form with the assistance of a necessary minimum quantity of an aqueous liquid, which gel remains visually distinguishable when introduced into a further quantity of an aqueous liquid.

For the purposes of the present invention, visually distinguishable means that the active ingredient-containing gel formed by extraction from the dosage form with the assistance of a necessary minimum quantity of aqueous liquid, when introduced with a hypodermic needle with a diameter of 0.9 mm into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 min.

The increase in viscosity of the gel with the assistance of the selected viscosity-increasing agent means that, although this has been rendered more difficult, the gel may still be passed through a needle or injected. It also means that when the resultant extract or gel is introduced at 37° C. into a further quantity of aqueous liquid, for example also by injection into blood, a largely cohesive thread is initially obtained which, while it may be broken up into smaller fragments by mechanical action, it cannot be dispersed or even dissolved in such a manner that it may safely be administered parenterally, in particular intravenously.

Intravenous administration of such an extract would most probably result in obstruction of blood vessels, associated with serious embolism or even death of the abuser.

For the purposes of the present invention, an extract or gel obtained from the dosage form according to the invention with the assistance of a necessary minimum quantity of an aqueous liquid, preferably water, is deemed to be passable through a needle if the gel formed in this manner can still be drawn up and injected back out of a hypodermic needle with a diameter of 2 mm, preferably of 1.5 mm, particularly preferably of 0.6 mm. Pharmaceutical active ingredients with potential for abuse are known to the person skilled in the art, as are the quantities thereof to be used and processes for the production thereof, and may be present in the dosage form according to the invention as such, in the form of corresponding derivatives, in particular esters or ethers, or in each case in the form of corresponding physiologically acceptable compounds, in particular in the form of the salts or solvates thereof. The dosage form according to the invention is also suitable for the administration of a plurality of active ingredients. It is preferably used for the administration of a single active ingredient.

The dosage form according to the invention is in particular suitable for preventing abuse of a pharmaceutical active ingredient selected from the group consisting of opiates, opioids, tranquillisers, preferably benzodiazepines, stimulants and other narcotics.

The dosage form according to the invention is very particularly preferably suitable for preventing abuse of an opiate, opioid, tranquilliser or another narcotic, which is selected from the group consisting of N-{1-[2-(4-Ethyl-5-oxo-2-tetrazolin-1-yl)ethyl]-4-methocxymethly-4-piperidyl}propionanilide(alfentanil), 5,5-diallylbarbituric acid(allobarbital, allylprodine, alphaprodine, 8-chloro-1-methyl-6-phenyl-4H-[1,2,4]triazolo[4,3-a][1,4]-benzodiazepine(alprazolam), 2-diethylaminopropiophenone(amfepramone), (±)-a-methylphenethylamine (amphetamine), 2-(a- methylphenethylamino)-2-phenylacetonitrile (amphetaminil), 5-ethyl-5-isopentylbarbituric acid (amobarbital), anileridine, apocodeine, 5,5-diethylbarbituric acid(barbital), benzylmorphine, bezitramide, 7-bromo-5-(2-pyridyl)-1H-1,4-benzodiazepine-2(3H)-one(bromazepam), 2-bromo-4-(2-chlorophenyl)-9-methyl-6H-thieno[3,2-n][1,2,4]triazolo[4,3-a][1,4]diazepine(brotizolam), 17-cyclopropylmethyl-4,5a-epoxy-7a[(S)-1-hydroxy-1,2,2-trimethylpropyl]-6-methoxy-6,14-endoethanomorphinan-3-ol (buprenorphine), 5-butyl-5-ethylbarbituric acid (butobarbitol), butorphanol, (7-chloro-1,3-dihydro-1-methyl-2-oxo-5-phenyl-2H-1,4-benzodiazepin-3-yl) dimethylcarbamate(camazepam), (1S,2S)-2-amino-1-phenyl-1-propanol (cathine/D-norpseudoephedrine), 7-chloro-N-methyl-5-phenyl-3H-1,4-benzodiazepin-2-ylamine 4-oxide(chlordiazepoxide), 7-chloro-1-methyl-5-phenyl-1H-1,5-benzodiazepine-2,4(3H,5H)-dione(clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one(clotiazepam), 10-chloro-11b-(2-chlorophenyl)-2,3,7,11b-tetrahydrooxazolo[3,2-d][1,4]benzodiazepin-6(5H)-one(cloxazolam), (−)-methyl-[3β benzoyloxy-2β(1aH,5aH)-tropane carboxylate](cocaine), 4,5a-epoxy-3-methoxy-17-methyl-7-morphinen-6a-ol(codeine), 5-(1-cyclohexenyl)-5-ethyl barbituric acid(cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl) propionate(dextropropoxyphene), dezocine, diampromide, diamorphone, 7-chloro-1-methyl-5-phenyl-1H-1,4-benzodiazepin-2(3H)-one(diazepam), 4,5a-epoxy-3-methoxy-17-methyl-6a-morphinanol(dihydrocodeine), 4,5a-epoxy-17-methyl-3,6a-morphinandiol(dihydromorphine), dimenoxadol, dimephetamol, dimethylthiambutene, dioxaphetyl butyrate, dipipanone, (6aR,10aR)-6,6,9-trimethyl-3-pentyl-6a,7,8,10a-tetrahydro-6H-benzo[c]chromen-1-ol (dronabinol), eptazocine, 8-chloro-6-phenyl-4H-[1,2,4]triazolo[4,3-(a)][1,4]benzodiazepine(estazolam), ethoheptazine, ethylmethylthiambutene, ethyl [7-chloro-5-(2-fluorophenyl)-2,3-dihydro-2-oxo-1H-1,4-benzodiazepine-3-carboxylate](ethyl loflazepate), 4,5a-epoxy-3-ethoxy-17-methyl-7-morphinen-6a-ol(ethylmorphine), etonitazene, 4,5a-epoxy-7a-(1-hydroxy-1-methylbutyl)-6-methoxy-17-methyl-6,1 4-endoetheno-morphinan-3-ol(etorphine), N-ethyl-3-phenyl-8,9,10-trinorbornan-2-ylamine (fencamfamine), 7-[2-(a-methylphenethylamino)ethyl]-theophylline)(fenethylline), 3-(a-methylphenethylamino) propionitrile(fenproporex), N-(1-phenethyl-4-piperidyl) propionanilide(fentanyl), 7-chloro-5-(2-fluorophenyl)-1-methyl-1H-1,4-benzodiazepin-2(3H)-one(fludiazepam), 5-(2-fluorophenyl)-1-methyl-7-nitro-1H-1,4-benzodiazepin-2(3H)-one(flunitrazepam), 7-chloro-1-(2-diethylaminoethyl)-5-(2-fluorophenyl)-1H-1,4-benzodiazepin-2(3H)-one(flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolyl[3,2-d][1,4]benzodiazepin-6(5H)-one(haloxazolam), heroin, 4,5a-epoxy-3-methoxy-17-methyl-6-morphinanone(hydrocodone), 4,5a-epoxy-3-hydroxy-17-methyl-6-morphinanone(hydromorphone), hydroxypethidine, isomethadone, hydroxymethylmorphinan, 11-chloro-8,1 2b-dihydro-2,8-dimethyl-1 2b-phenyl-4H-[1,3]oxazino[3,2-d][1,4]benzodiazepine-4,7(6H)-dione (ketazolam), 1-[4-(3-hydroxyphenyl)-1-methyl-4-piperidyl]-1-propanone(ketobemidone), (3S,6S)-6-dimethylamino-4,4-diphenylheptan-3-yl acetate (levacetylmethadol(LAAM)), (−)-6-dimethylamino-4,4-diphenol-3-heptanone(levomethadone), (−)-17-methyl-3-morphinanol(levorphanol), levophenacylmorphane, lofentanil, 6-(2-chlorophenyl)-2-(4-methyl-1-piperazinylmethylene)-8-nitro-2H-imidazo[1,2-a][1,4]-benzodiazepin-1 (4H)-one(loprazolam), 7-chloro-5-(2-chlorophenyl)-3-hydroxy-1H-1,4-benzodiazepin-2(3H)-one(lorazepam), 7-chloro-5-(2-chlorophenyl)-3-hydroxy-1-methyl-1H-1,4-benzodiazepin-2(3H)-one(lormetazepam), 5-(4-chlorophenyl)-2,5-dihydro-3H-imidazo[2,1-a]isoindol-5-ol(mazindol), 7-chloro-2,3-dihydro-1-methyl-5-phenyl-1H-1,4-benzodiazepine(medazepam), N-(3-chloropropyl)-a-methylphenethylamine(mefenorex), meperidine, 2-methyl-2-propyltrimethylene dicarbamate(meprobamate), meptazinol, metazocine, methylmorphine, N,a-dimethylphenethylamine(metamphetamine), (±)-6-dimethylamino-4,4-diphenol-3-heptanone(methadone), 2-methyl-3-o-tolyl-4(3H)-quinazolinone(methaqualone), methyl[2-phenyl-2-(2-piperidyl)acetate](methylphenidate), 5-ethyl-1-methyl-5-phenylbarbituric acid(methylphenobarbital), 3,3-diethyl-5-methyl-2,4-piperidinedione(methyprylon), metopon, 8-chloro-6-(2-fluorophenyl)-1-methyl-4H-imidazo[1,5-a][1,4]benzodiazepine(midazolam), 2-(benzhydrylsulfinyl)acetamide(modafinil), 4,5a-epoxy-17-methyl-7-morphinen-3,6a-diol(morphine), myrophine, (±)-trans-3-(1,1-dimethylheptyl)-7,8,10,10a-tetrahydro-1-hydroxy-6,6-dimethyl-6H-dibenzo-[b,d]pyran-9(6aH)-one(nabilone), nalbuphene, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one(nitrazepam), 7-chloro-5-phenyl-1H-1,4-benzodiazepin-2(3H)-one(nordazepam), norlevorphanol, 6-dimethylamino-4,4-diphenyl-3-hexanone(normethadone), normorphine, norpipanone, the exudation from plants belonging to the species *Papaver somniferum* (opium), 7-chloro-3-hydroxy-5-phenyl-1H-1,4-benzodiazepin-2 (3H)-one(oxazepam), (cis-trans)-10-chloro-2,3,7,11b-tetrahydro-2-methyl-11b-phenyloxazolo[3,2-d][1,4]benzodiazepin-6-(5H)-one(oxazolam), 4,5a-epoxy-1 4-hydroxy-3-methoxy-17-methyl-6-morphinanone(oxycodone), oxymorphone, plants and parts of plants belonging to the species *Papaver somniferum* (including the subspecies *setigerum*) (*Papaver somniferum*), papaveretum, 2-imino-5-phenyl-4-oxazolidinone(pernoline), 1,2,3,4,5,6-hexahydro-6,11-dimethyl-3-(3-methyl-2-butenyl)-2,6-methano-3-benzazocin-8-ol(pentazocine), 5-ethyl-5-(1-methylbutyl)-barbituric acid(pentobarbital), ethyl-(1-methyl-4-phenyl-4-piperidinecarboxylate)(pethidine), phenadoxone, phenomorphane, phenazocine, phenoperidine, piminodine, pholcodeine, 3-methyl-2-phenylmorpholine (phenmetrazine), 5-ethyl-5-phenylbarbituric acid(phenobarbital), a,a-dimethylphenethylamine(phentermine), 7-chloro-5-phenyl-1-(2-propynyl)-1H-1,4-benzodiazepin-2(3H)-one (pinazepam), a-(2-piperidyl)benzhydryl alcohol(pipradrol), 1'-(3-cyano-3,3-diphenylpropyl)[1,4'-bipiperidine]-4'-carboxamide(piritramide), 7-chloro-1-(cyclopropylmethyl)-5-phenyl-1H-1,4-benzodiazepin-2(3H)-one(prazepam), profadol, proheptazine, promedol, properidine, propoxyphene, N-(1-methyl -2-piperidinoethyl)-N-(2-pyridyl)propionamide, methyl {3-[4-methoxycarbonyl-4-(N-phenylpropanamido)piperidino]propanoate}(remifentanil), 5-sec-butyl-5-ethylbarbituric acid(secbutabarbital), 5-allyl-5-(1-methylbutyl)-barbituric acid(secobarbital), N-{4-methoxymethyl-1-[2-(2-thienyl)ethyl]-4-piperidyl}propionanilide (sufentanil), 7-chloro-2-hydroxymethyl-5-phenyl-1H-1,4-benzodiazepin-2(3H)-one (temazepam), 7-chloro-5-(1-cyclohexenyl)-1-methyl-1H-1,4-benzodiazepin-2(3H)-one(tetrazepam), ethyl(2-dimethylamino-1-phenyl-3-cyclohexene-1-carboxylate)(tilidine, cis and trans)), tramadol, 8-chloro-6-(2-chlorophenyl)-1-methyl-4H-[1,2,4]triazolo[4,3-a][1,4]benzodiazepine(triazolam), 5-(1-methylbutyl)-5-vinylbarbituric acid(vinylbital), (1R*,2R*)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl)cyclohexanol and for corresponding stereoisomeric compounds, the corresponding derivatives thereof in each case, in particular esters or ethers, and the physiologically acceptable compounds thereof in each case, in particular the salts and solvates thereof.

The compounds (1R,2R*)-3-(3-dimethylamino-1-ethyl-2-methyl-propyl)-phenol and (1R,2R,4S)-2-(dimethylamino)methyl-4-(p-fluorobenzyloxy)-1-(m-methoxyphenyl)cyclohexanol, the physiologically acceptable compounds thereof, in particular the hydrochlorides thereof and processes for the production thereof are respectively known, for example, from EP-A-693475 and EP-A-780369. The corresponding descriptions are hereby introduced as a reference and are deemed to be part of the disclosure.

In order to verify whether a viscosity-increasing agent is suitable for use in the dosage form according to the invention, said agent is first formulated in a corresponding dosage form in quantities such that there is no appreciable (±5%) influence on active ingredient release relative to a dosage form without viscosity-increasing agent. The corresponding dosage form is moreover comminuted, preferably ground, and extracted with 10 ml water at 25° C. If a gel is furthermore formed which meets the above-stated conditions, the corresponding viscosity-increasing agent is suitable for the production of a dosage form according to the invention.

Preferably, one or more viscosity-increasing agents are used in the dosage form according to the invention, said agents being selected from the group consisting of microcrystalline cellulose with 11 wt. % carboxymethylcellulose sodium (Avicel® RC 591), carboxymethylcellulose sodium (Blanose®, CMC—Na C3001P®, Frimulsion BLC-5®, Tylose C300 P®), polyacrylic acid (Carbopol® 980 NF, Carbopol® 981), locust bean flour (Cesagum® LA-200, Cesagum® LID/150, Cesagum® LN-1), pectins, preferably from citrus fruits or apples (Cesapectin® HM Medium Rapid Set), waxy maize starch (C*Gel 04201®), sodium alginate (Frimulsion ALG (E401)®), guar flour (Frimulsion BM®, Polygum 2611-75®), iota-carrageenan (Frimulsion D021®), karaya gum, gellan gum (Kelcogel F®, Kelcogel LT100®), galactomannan (Meyprogat 150®), tara stone flour (Polygum 4311®), propylene glycol alginate (Protanal-Ester SD-LB®), sodium hyaluronate, tragacanth, tara gum (Vidogum SP 200®), fermented polysaccharide welan gum (K1A96), xanthans such as xanthan gum (Xantural 180®). The names stated in brackets are the trade names by which the materials are known commercially.

In general, a quantity of 0.1 to 25 wt. %, preferably of 0.5 to 15 wt. %, particularly preferably of 1-10 wt. % of the viscosity-increasing agent, relative to the total formulation, is sufficient in order to meet the above-stated conditions. The viscosity-increasing agents are preferably present in the dosage form according to the invention in quantities of=5 mg, particularly preferably of=10 mg per dosage form, i.e. per administration unit.

In a particularly preferred embodiment of the present invention, the viscosity-increasing agents used are those which, in addition to the above-stated conditions, also form a gel which encloses air bubbles on extraction from the dosage form with the necessary minimum quantity of aqueous liquid. The resultant gels are distinguished by a turbid appearance, which provides the potential abuser with an additional optical warning and discourages him/her from administering the gel parenterally.

The active ingredient or ingredients with potential for abuse and the viscosity-increasing agents and optionally physiologically acceptable auxiliary substances may be formulated to yield the dosage form according to the invention in accordance with conventional methods known to the person skilled in the art. Corresponding methods for formulating the dosage form according to the invention are known per se to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

Surprisingly, due to the inventive selection of the viscosity-increasing agents, it is possible to combine the active ingredients and the viscosity-increasing agents in the dosage form according to the invention without spatial separation from one another, without there being any impairment of release of the active ingredient from the correctly administered dosage form relative to a corresponding dosage form which does not comprise the viscosity-increasing agent.

Obviously, however, it is also possible to combine the viscosity-increasing agents and the active ingredients in the dosage form in a mutually spatially separated arrangement.

The parenteral abuse-proofed solid dosage forms according to the invention are preferably suitable for oral or rectal administration, particularly preferably for oral administration.

Where the dosage form according to the invention is intended for rectal administration, it preferably assumes the form of a suppository.

If the dosage form according to the invention is intended for oral administration, it preferably assumes the form of a tablet, a capsule or of an oral osmotic therapeutic system (OROS).

Oral osmotic therapeutic systems and suitable materials and processes for the production thereof are known per se to the person skilled in the art, for example from U.S. Pat. No. 4,612,008, U.S. Pat. No. 4,765,989 and U.S. Pat. No. 4,783,337. The corresponding descriptions are hereby introduced as a reference and are deemed to be part of the disclosure. The corresponding oral osmotic therapeutic system may preferably assume the form of a single or twin chamber system, in each case with a single layer or multilayer structure. In these systems, the push layer, i.e. the layer which produces the osmotic pressure by swelling, by means of which the overlying layer is expelled from the system, preferably at least in part consists of the viscosity-increasing agents used according to the invention.

In a further preferred embodiment of the present invention, the orally administrable dosage form according to the invention assumes multiparticulate form containing in each case the complete mixture of active ingredient and viscosity-increasing agent, preferably in the form of microtablets, microcapsules, micropellets, granules, spheroids, beads or pellets, preferably packaged in capsules or press-moulded into tablets The multiparticulate forms preferably have a size in the range from 0.1 to 3 mm, particularly preferably in the range from 0.5 to 2 mm.

The dosage form according to the invention may preferably also comprise one or more active ingredients, blended with the viscosity-increasing agent, at least in part in delayed-release form, wherein delayed release may be achieved with the assistance of conventional materials and processes known to the person skilled in the art, for example by embedding the active ingredient in a delayed-release matrix or by applying one or more delayed-release coatings.

Delayed release of the active ingredient may preferably also be achieved by purposeful selection of one or more of the above-stated viscosity-increasing agents in suitable quantities as the matrix material. The person skilled in the art may determine the agents and the quantity thereof suitable for the particular desired release by simple preliminary testing, wherein it must, of course, be ensured that, as described above, gel formation occurs when the attempt is made to abuse the resultant dosage form.

In any event, it must be ensured that the delayed-release auxiliary substances, and likewise further optionally present auxiliary substances, do not interfere with gel formation or impair the stability of the gel which is formed.

If the dosage form according to the invention is intended for oral administration, it may also comprise a coating which is resistant to gastric juices and dissolves as a function of the pH value of the release environment.

By means of this coating, it is possible to ensure that, when correctly administered, the dosage form according to the invention passes through the stomach undissolved and the active ingredient is only released in the intestines. The coating which is resistant to gastric juices preferably dissolves at a pH value of between 5 and 7.5.

Corresponding materials and methods for the controlled release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

In a further preferred embodiment, the dosage form according to the invention contains the active ingredient not only in its delayed-release form, but also in its non-delayed-release form. By combination with the immediately released active ingredient, it is possible to obtain an initial dose for rapid pain relief. The slow release from the delayed-release form then prevents any rapid decline in action.

The invention is explained below with reference to Examples. These explanations are given merely by way of example and do not restrict the general concept of the invention.

EXAMPLES

Example 1

Matrix tablets with the following composition per tablet

| | |
|---|---|
| (−)-(1R,2R)-3-(3-Dimethylamino-1-ethyl-2-methyl-propyl)phenol hydrochloride | 100 mg |
| Hydroxypropylmethylcellulose (Metolose 90 SH 100,000 from Shinetsu), 100,000 mPa·s | 70 mg |
| Xanthan, NF | 10 mg |
| Microcrystalline cellulose (Avicel PH 102 from FMC) | 123 mg |
| Highly disperse silicon dioxide | 4 mg |
| Magnesium stearate | 3 mg |
| Total quantity | 310 mg | were produced in the following manner in a batch size of 1000 tablets: All the constituents were weighed out and screened in Quadro Comil U10 screening machine using a screen size of 0.813 mm, mixed in a container mixer (Bohle LM 40) for 15 min±15 s at a rotational speed of 20±1 rpm and pressed on a Korsch EKO eccentric press to form biconvex tablets with a diameter of 10 mm, a radius of curvature of 8 mm and an average tablet weight of 310 mg.

In vitro release was determined using the Ph. Eur. paddle method at 75 rpm in 900 ml of pH 6.8 buffer to Ph. Eur. at 37° C., with detection by UV spectrometry, and is shown in the following Table, together with a comparison with a corresponding tablet with 80 mg of hydroxypropylmethylcellulose ("HPMC") without addition of xanthan.

| Time [min] | Total quantity of active ingredient released [%] from tablets according to Example 1 (70 mg HPMC + 10 mg xanthan) | Total quantity of active ingredient released [%] from tablets with 80 mg HPMC (without xanthan) |
|---|---|---|
| 0 | 0 | 0 |
| 30 | 19 | 18 |
| 240 | 62 | 59 |
| 480 | 83 | 80 |
| 600 | 88 | 87 |
| 720 | 93 | 93 |

One of the tablets containing xanthan was ground and shaken with 10 ml of water. A viscous, turbid suspension formed. Once the coarse, solid components of the suspension had settled out, the gel which had formed was drawn up into a syringe with a 0.9 mm diameter needle. The drawn up gel was injected into water at 37° C. and threads, which did not mix with the water, with the diameter of the needle remained clearly discernible While the threads could be broken up by stirring, they could not be dissolved and the thread fragments remained visible to the naked eye. Were such an extract to be injected into blood vessels, vessel blockages would occur.

Example 2

Comparative Example Regarding Very Poor Needle Passage Properties?

Matrix tablets with the following composition per tablet

| | |
|---|---|
| (−)-(1R,2R)-3-(3-Dimethylamino-1-ethyl-2-methyl-propyl)phenol hydrochloride | 100 mg |
| Hydroxypropylmethylcellulose (Metolose 90 SH 100,000 from Shinetsu), 100,000 mPa·s | 40 mg |
| Xanthan, NF | 40 mg 12% ? |
| Microcrystalline cellulose (Avicel PH 102 from FMC) | 123 mg |
| Highly disperse silicon dioxide | 4 mg |
| Magnesium stearate | 3 mg |
| Total quantity | 310 mg | were produced as stated in Example 1 and their release characteristics were investigated.

| Time [min] | Total quantity of active ingredient released [%] |
|---|---|
| 0 | 0 |
| 30 | 19 |
| 240 | 61 |
| 480 | 81 |
| 600 | 87 |
| 720 | 91 |

One of the tablets was ground and shaken with 10 ml of water. A viscous, turbid suspension with enclosed air bubbles formed, the viscosity of which was greater than in Example 1. Once the coarse, solid components of the suspension had settled out, the gel which had formed was drawn up into a syringe with a 0.9 mm diameter needle. The drawn up gel was injected into water at 37° C. and threads, which did not mix with the water, with the diameter of the needle were clearly discernible. While the threads could be broken up by stirring, they could not be dissolved and the thread fragments remained visible to the naked eye. Were such a gel to be injected into blood vessels, vessel blockages would occur.

Example 3

Matrix tablets with the following composition per tablet

| | |
|---|---|
| (−)-(1R,2R)-3-(3-dimethylamino-1-ethyl-2-methyl-propyl)phenol hydrochloride | 100 mg |
| Xanthan, NF | 80 mg |
| Microcrystalline cellulose (Avicel PH 102 from FMC) | 123 mg |
| Highly disperse silicon dioxide | 4 mg |
| Magnesium stearate | 3 mg |
| Total quantity | 310 mg | were produced as stated in Example 1.

One of these tablets was ground and shaken with 10 ml of water. A viscous, turbid suspension, which had enclosed air bubbles, formed, the viscosity of which was higher than in Example 1. Once the coarse, solid components of the suspension had settled out, the gel which had formed was drawn up into a syringe with a 0.9 mm diameter needle. The drawn up gel was injected into water at 37° C. and clearly discernible threads, which did not mix with the water, with the diameter of the needle were visible. While the threads could be broken up by stirring, they could not be dissolved and the thread fragments remained visible to the naked eye. Were such a gel to be injected into blood vessels, vessel blockages would occur.

Examples 4-7

Matrix tablets with the following composition per tablet

| Example | 4 | 5 | 6 | 7 |
|---|---|---|---|---|
| (−)-(1R,2R)-3-(3-Dimethylamino-1-ethyl-2-methyl-propyl)phenol hydrochloride | 100 mg | 100 mg | 100 mg | 100 mg |
| Hydroxypropylmethylcellulose (Metolose 90 SH 100,000 from Shinetsu), 100,000 mPa·s | 80 mg | 80 mg | 80 mg | 80 mg |
| Carboxymethylcellulose (Tylose C300) | 10 mg | | | |
| Carboxymethylcellulose (Tylose C600) | | 10 mg | | |
| Hydroxyethylcellulose (Tylose H300) | | | 10 mg | |
| Hydroxyethylcellulose (Tylose H4000) | | | | 10 mg |
| Microcrystalline cellulose (Avicel PH 102 from FMC) | 123 mg | 123 mg | 123 mg | 123 mg |
| Highly disperse silicon dioxide | 4 mg | 4 mg | 4 mg | 4 mg |
| Magnesium stearate | 3 mg | 3 mg | 3 mg | 3 mg |
| Total quantity | 320 mg | 320 mg | 320 mg | 320 mg | were produced as stated in Example 1.

One of each of these tablets was ground and shaken with 10 ml of water. A viscous, turbid suspension with enclosed air bubbles formed. Once the coarse, solid components of the suspension had settled out, the [gel] was drawn up into a syringe with a 0.9 mm diameter needle. The drawn up gel was injected into water at 37° C. and clearly visible threads, which did not mix with the water, with the diameter of the needle remained discernible. While the threads could be broken up by stirring, they could not be dissolved and the thread fragments remained visible to the naked eye. Were such a gel to be injected into blood vessels, vessel blockages would occur.

Examples 8-13

Matrix tablets with the following composition per tablet

| Example | 8 | 9 | 10 | 11 | 12 | 13 |
|---|---|---|---|---|---|---|
| Morphine sulfate pentahydrate | 60 mg | 60 mg | 60 mg | 60 mg | 60 mg | 60 mg |
| Hydroxypropylmethylcellulose (Metolose 90 SH 15,000 from Shinetsu), 15,000 mPa · s | 60 mg | 60 mg | 60 mg | 60 mg | 60 mg | 60 mg |
| Xanthan, NF | 10 mg | 30 mg | | | | |
| Carboxymethylcellulose (Tylose C300) | | | 10 mg | | | |
| Carboxymethylcellulose (Tylose C600) | | | | 10 mg | | |
| Hydroxyethylcellulose (Tylose H300) | | | | | 10 mg | |
| Hydroxyethylcellulose (Tylose H4000) | | | | | | 10 mg |
| Microcrystalline cellulose (Avicel PH 102 from FMC) | 123 mg | 123 mg | 123 mg | 123 mg | 123 mg | 123 mg |
| Highly disperse silicon dioxide | 4 mg | 4 mg | 4 mg | 4 mg | 4 mg | 4 mg |
| Magnesium stearate | 3 mg | 3 mg | 3 mg | 3 mg | 3 mg | 3 mg |

One of each of these tablets was ground and shaken with 10 ml of water. A viscous, turbid suspension with enclosed air bubbles formed. Once the coarse, solid components of the suspension had settled out, the [gel] was drawn up into a syringe with a 0.9 mm diameter needle. The drawn up gel was injected into water at 37° C. and clearly visible threads, which did not mix with the water, with the diameter of the needle remained discernible. While the threads could be broken up by stirring, they could not be dissolved and the thread fragments remained visible to the naked eye. Were such a gel to be injected into blood vessels, vessel blockages would occur.

Examples 14-18

Capsules with the following composition of the simple powder mixture per capsule (size 4 capsule)

| Example | 14 | 15 | 16 | 17 | 18 |
|---|---|---|---|---|---|
| Morphine sulfate pentahydrate | 20 mg | 20 mg | 20 mg | 20 mg | 20 mg |
| Xanthan, NF | 10 mg | | | | |
| Carboxymethylcellulose (Tylose C300) | | 10 mg | | | |
| Carboxymethylcellulose (Tylose C600) | | | 10 mg | | |
| Hydroxyethylcellulose (Tylose H300) | | | | 10 mg | |
| Hydroxyethylcellulose (Tylose H4000) | | | | | 10 mg |
| Microcrystalline cellulose (Avicel PH 102 from FMC) | 68 mg | 68 mg | 68 mg | 68 mg | 68 mg |
| Highly disperse silicon dioxide | 1 mg | 1 mg | 1 mg | 1 mg | 1 mg |
| Magnesium stearate | 1 mg | 1 mg | 1 mg | 1 mg | 1 mg |

One of each of these tablets was ground and shaken with 10 ml of water. A viscous, turbid suspension with enclosed air bubbles formed. Once the coarse, solid components of the suspension had settled out, the [gel] was drawn up into a syringe with a 0.9 mm diameter needle. The drawn up gel was injected into water at 37° C. and clearly visible threads, which did not mix with the water, with the diameter of the needle remained discernible. While the threads could be broken up by stirring, they could not be dissolved and the thread fragments remained visible to the naked eye. Were such a gel to be injected into blood vessels, vessel blockages would occur.

The invention claimed is:

1. A parenteral abuse-proofed solid dosage form for oral administration, comprising, in addition to one or more active ingredients with potential for abuse selected from the group consisting of opiates, opioids, tranquillizers, stimulants and narcotics, at least one viscosity-increasing agent in a quantity equal to or greater than 5 mg per dosage form and such that an aqueous extract obtained from the dosage form with 10 ml of water at 25° C. forms a gel which can still pass through a needle having a diameter of 0.9 mm and remains visually distinguishable when introduced by a needle into a further quantity of an aqueous liquid.

2. A dosage form according to claim 1, wherein the active ingredient is an opiate, opioid, tranquillizer or a narcotic selected from the group consisting of N-{1-[2-(4-Ethyl-5-oxo-2-tetrazolin-1-yl)ethyl]-4-methoxymethyl-4-piperidyl}propionanilide(alfentanil), 5,5-diallylbarbituric acid(allobarbital), allylprodine, alphaprodine, 8-chloro-1-methyl-6-phenyl-4H-[1,2,4]triazolo[4,3-a][1,4]-benzodiazepine(alprazolam), 2-diethylaminopropiophenone(amfepramone), (.+-.)-.alpha.-methylphenethylamine (amphetamine), 2-(.alpha.-methylphenet-hylamino)-2-phenylacetonitrile(amphetaminil), 5-ethyl-5-isopentylbarbituri- c acid(amobarbital), anileridine, apocodeine, 5,5-diethylbarbituric acid(barbital), benzylmorphine, bezitramide, 7-bromo-5-(2-pyridyl)-1H-1,4-benzodiazepine-2(3H)-one (bromazepam), 2-bromo-4-(2-chlorophenyl)-9-methyl-l-6H-thieno[3,2-f][1,2,4]triazolo[4,3-a][1,4]diazepine(brotizolam), 17-cyclopropylmethyl-4,5a-epoxy-7a[(S)-1-hydroxy-1,2,2-trimethyl-propyl]--6-methoxy-6,14-endo-ethanomorphinan-3-ol(buprenorphine), 5-butyl-5-ethylbarbituric acid(butobarbital), butorphanol, (7-chloro-1,3-dihydro-1-methyl-2-oxo-5-phenyl-2H-1,4-benzodiazepin-3-yl)dimethylcarbamate (camazepam), (1S,2S)-2-amino-1-phenyl-1-propanol (cathine/D- -norpseudoephedrine), 7-chloro-N-methyl-5-phenyl-3H-1,4-benzodiazepin-2-yl-amine 4-oxide (chlordiazepoxide), 7-chloro-1-methyl-5-phenyl-1H-1,5-benzodi-azepine-2,4(3H,5H)-dione(clobazam), 5-(2-chlorophenyl)-7-nitro-1H-1,4-benz-odiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e][1,4]diazepin-2(3H)-one(clotiazepam), 10-chloro-11b-(2-chlorophenyl)-2,3,7,11b-tetrahydroox-azol-o [3,2-d][1,4]benzodiazepin-6 (5H)-one(cloxazolam), (−)-methyl-[3.beta.-benzoyloxy-2.beta.(1.alpha.H,5.alpha.H)-tropane carboxylate](cocaine), 4,5.alpha.-epoxy-3-methoxy-17-methyl-7-morphinen-6.alpha.-ol(codeine), 5-(1-cyclohexenyl)-5-ethyl barbituric acid(cyclobarbital), cyclorphan, cyprenorphine, 7-chloro-5-(2-chlorophenyl)-1H-1,4-benzodiazepin-2(3H)-one(delorazepam), desomorphine, dextromoramide, (+)-(1-benzyl-3-dimethylamino-2-methyl-1-phenylpropyl)pro-pionate(dextropropoxyphene), dezocine, diampromide, diamorphone, 7-chloro-1-methyl-5-phenyl-1H-1,4-benzodiazepin-2(3H)-one (diazepam), 4,5.alpha.-epoxy-3-methoxy-17-methyl-6.alpha.-morphinanol(dihydrocodeine)-, 4,5.alpha.-epoxy-17-methyl-3,6a-morphinandiol(dihydromorphine), dimenoxadol, dimephetamol, dimethylthiambutene, dioxaphetyl butyrate, dipipanone, (6aR,10aR)-6,6,9-trimethyl-3-pentyl-6a,7,8,10a-tetrahydro-6H-benzo[c]chromen-1-ol(dronabinol), eptazocine, 8-chloro-6-phenyl-4H-[1,2,4]-triazolo[4,3-(a)][1,4]benzodiazepine(estazolam), ethoheptazine, ethylmethylthiambutene, ethyl[7-chloro-5-(2-fluorophenyl)-2,3-dihydro-2-oxo-1H-1,4-benzodiazepine-3-carboxylate](ethyl loflazepate), 4,5.alpha.-epoxy-3-ethoxy-17-methyl-7-morphinen-6.alpha.-ol(ethylmorphine-), etonitazene, 4,5.alpha.-epoxy-7.alpha.-(1-hydroxy-1-methylbutyl)-6-meth-oxy-17-methyl-6,14-endo-etheno-morphinan-3-ol(etorphine), N-ethyl-3-phenyl-8,9,10-trinorbornan-2-ylamine (fencamfamine), 7-[2-(.alpha.-methylphenethylamino)ethyl]-theophylline)(fenethylline), 3-(.alpha.-methylphenethylamino) propionitrile(fenproporex), N-(1-phenethyl-4-piperidyl) propionanilide(fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one(flunitrazepam), 7-chloro-1-(2-diethylaminoethyl)-5-(2-fluorophenyl)-1H-1,4-benzodiazepin-2(3H)-one(flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3]oxazolyl[3,2-d][1,-4]benzodiazepin-6(5H)-one (haloxazolam), heroin, 4,5.alpha.-epoxy-3-methox-y-17-methyl-6-morphinanone(hydrocodone), 4,5.alpha.-epoxy-3-hydroxy-17-methyl-6-morphinanone (hydromorphone), hydroxypethidine, isomethadone, hydroxymethylmorphinan, 11-chloro-8,12b-dihydro-2,8-dimethyl-12b-phenyl-4H-[1,3]oxazino[3,2-d][1,4]benzodiazepine-4,7(6H)-dione(ketazolam), 1-[4-(3-hydroxyphenyl)-1-methyl-4-piperidyl]-1-propanone(ketobemidone), (3S,6S)-6-dimethylamino-4,4-diphenylheptan-3-yl acetate (levacetylmethadol(LAAM)), (−)-6-dimethylamino-4,4-diphenol-3-heptanone(l-evomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a][1,4]-benzodiazepin-1(4H)-one(lop-razolam), 7-chloro-5-(2-chlorophenyl)-3-hydroxy-1H-1,4-benzodiazepin-2(3H)-one(lorazepam), 7-chloro-5-(2-chlorophenyl)-3-hydroxy-1-methyl-1H-1,4-ben-zodiazepin-2(3H)-one(lormetazepam), 5-(4-chlorophenyl)-2,5-dihydro-3H-imid-azo[2,1-a]isoindol-5-ol (mazindol), 7-chloro-2,3-dihydro-1-methyl-5-phenyl- -1H-1,4-benzodiazepine(medazepam), N-(3-chloropropyl)-.alpha.-methylphenet-hylamine(mefenorex), meperidine, 2-methyl-2-propyltrimethylene dicarbamate (meprobamate), meptazinol, metazocine, methylmorphine, N,.alpha.-dimethylphenethylamine(metamphetamine), (.+−.)-6-dimethylamino-4,4-diphenol-3-heptanone(methadone), 2-methyl-3-o-tolyl-4(3H)-quinazolinon-e(methaqualone), methyl [2-phenyl-2-(2-piperidyl)acetate](methylphenidate)-, 5-ethyl-1-methyl-5-phenylbarbituric acid(methylphenobarbital), 3,3-diethyl-5-methyl-2,4-piperidinedione(methyprylon), metopon, 8-chloro-6-(2-fluorophenyl)-1-methyl-4H-imidazo[1,5-a][1,4]benzodiazepine-(midazolam), 2-(benzhydrylsulfinyl)acetamide(modafinil), 4,5.alpha.-epoxy-17-methyl-7-morphinen-3,6.alpha.-diol(morphine), myrophine, (.+−.)-trans-3-(1,1-dimethylheptyl)-7,8,10,10.alpha.-tetrahydr-o-1-hydroxy-6,6-dimethyl-6H-dibenzo-[b,d]pyran-9(6.alpha.H)-one(nabilone), nalbuphene, nalorphine, narceine, nicomorphine, 1-methyl-7-nitro-5-phenyl--1H-1,4-benzodiazepin-2(3H)-one(nimetazepam), 7-nitro-5-phenyl-1H-1,4-benz-odiazepin-2(3H)-one(nitrazepam), 7-chloro-5-phenyl-1H-1,4-benzodiazepin-2(−3H)-one(nordazepam), norlevorphanol, 6-dimethylamino-4,4-diphenyl-3-hexano ne(normethadone), normorphine, norpipanone, the exudation from plants belonging to the species *Papaver somniferum* (opium), 7-chloro-3-hydroxy-5-phenyl-1H-1,4-benzodiazepin-2(3H)-one(oxazepam), (cis-trans)-10-chloro-2,3,7,11b-tetrahydro-2-methyl-11b-phenyloxazolo[3,2- -d][1,4]benzodiazepin-6-(5H)-one(oxazolam), 4,5.alpha.-epoxy-14-hydroxy-3--methoxy-17-methyl-6-morphinanone (oxycodone), oxymorphone, plants and parts of plants belonging to the species *Papaver somniferum* (including the subspecies *setigerum*) (*Papaver somniferum*), papaveretum, 2-imino-5-phenyl-4-oxazolidinone(pemoline), 1,2,3,4,5,6-hexahydro-6,11-d- imethyl-3-(3-methyl-2-butenyl)-2,6-methano-3-benzazocin-8-ol(pentazocine), 5-ethyl-5-(1-methylbutyl)-barbituric acid(pentobarbital), ethyl-(1-methyl-4-phenyl-4-piperidinecarboxylate)(pethidine), phenadoxone, phenomorphane, phenazocine, phenoperidine, piminodine, pholcodine, 3-methyl-2-phenylmorpholine(phenmetrazine), 5-ethyl-5-phenylbarbituric acid(phenobarbital), .alpha., .alpha.-dimethylphenethylamine(phentermine), 7-chloro-5-phenyl-1-(2-propynyl)-1H-1,4-benzodiazepin-2(3H)-one(pinazepam), .alpha.-(2-piperidyl)benzhydryl alcohol(pipradrol), 1'-(3-cyano-3,3-diphenylpropyl)[1,4'-bipiperidine]-4'- -carboxamide(piritramide), 7-chloro-1-(cyclopropylmethyl)-5-phenyl-1H-1,4--benzodiazepin-2(3H)-one(prazepam), profadol, proheptazine, promedol, properidine, propoxyphene, N-(1-methyl -2-piperidinoethyl)-N-(2-pyridyl)p- ropionamide, methyl {3-[4-methoxycarbonyl-4-(N-phenylpropanamido)piperidin-o]pro-panoate}(remifentanil), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl)ethyl]-4-piperidyl}propionanilide (sufentanil), 7-chloro-2-hydroxy-methyl-5-phenyl-1H-1,4-be-nzodiazepin-2(3H)-one (temazepam), 7-chloro-5-(1-cyclohexenyl)-1-methyl-1H--1,4-benzodiazepin-2(3H)-one(tetrazepam), ethyl (2-dimethylamino-1-phenyl-3- -cyclohexene-1-carboxylate) (tilidine (cis and trans)), tramadol, 8-chloro-6-(2-chlorophenyl)-1-methyl-4H-[1,2,4]triazolo[4,3-a][1,4]benzod- iaz-epine(triazolam), 5-(1-methylbutyl)-5-vinylbarbituric acid (vinylbital), (1R*,2R*)-3-(3-dimethylamino-1-ethyl-2-methyl-propyl)-phenol, (1R,2R,4S)-2-(dimethylamino)

methyl-4-(p-fluorobenzyloxy)-1-(m-methoxyphenyl) cyclohexanol and corresponding stereoisomeric compounds in each case and the corresponding derivatives thereof in each case, in particular esters or ethers, and the physiologically acceptable compounds thereof in each case, in particular salts and solvates.

3. A dosage form according to claim 1, comprising a stimulant selected from the group consisting of amphetamine, norpseudoephedrine, methylphenidate and in each case optionally the corresponding physiological compounds thereof, in particular the bases, salts and solvates thereof.

4. A dosage form according to claim 1, comprising one or more viscosity-increasing agents selected from the group consisting of microcrystalline cellulose with 11 wt. % carboxymethylcellulose sodium (Avicel.RTM. RC 591), carboxymethylcellulose sodium (Blanose.RTM., CMC—Na C300P.RTM., Frimulsion BLC-5.RTM., Tylose C300 P.RTM.), polyacrylic acid (Carbopol.RTM. 980 NF, Carbopol.RTM. 981), locust bean flour (Cesagum.RTM. LA-200, Cesagum.RTM. LID/150, Cesagum.RTM. LN-1), citrus pectin (Cesapectin.RTM. HM Medium Rapid Set), waxy maize starch (C*Gel 04201.RTM.), sodium alginate (Frimulsion ALG (E401).RTM.), guar flour (Frimulsion BM.RTM., Polygum 26/1-75.RTM.), iota-carrageenan (Frimulsion D021.RTM.), karaya gum, gellan gum (Kelcogel F.RTM., Kelcogel LT100.RTM.), galactomannan (Meyprogat 150.RTM.), tara stone flour (Polygum 43/1.RTM.), propylene glycol alginate (Protanal-Ester SDLB.RTM.), apple pectin, lemon peel pectin, sodium hyaluronate, tragacanth, tara gum (Vidogum SP 200.RTM.), fermented polysaccharide welan gum (K1A96) and xanthan gum (Xantural 180.RTM.).

5. A dosage form according to claim 1, in particulate form.

6. A dosage form according to claim 1, comprising at least one active ingredient at least partially in controlled release form.

7. A dosage form according to claim 1, comprising a coating resistant to gastric juices.

8. The dosage form of claim 1, wherein said tranquilizer is benzodiazepine.

9. A dosage form according to claim 1, comprising the at least one viscosity-increasing agent in a quantity of $\geq 5$ mg per administration unit.

10. A dosage form according to claim 1 in multiparticulate form.

11. A dosage form according to claim 10, wherein said multiparticulate form is in the form of microtablets, microcapsules, micropellets, granules, spheroids, beads or pellets.

12. A dosage form according to claim 11 packaged in capsules or press-moulded into tablets.

* * * * *